(12) United States Patent
Migachyov

(10) Patent No.: US 6,183,413 B1
(45) Date of Patent: Feb. 6, 2001

(54) VALVE FOR BLADDER CONTROL DEVICE

(75) Inventor: Valery Migachyov, San Antonio, TX (US)

(73) Assignee: HK Medical Technologies Incorporated, San Antonio, TX (US)

( * ) Notice: Under 35 U.S.C. 154(b), the term of this patent shall be extended for 0 days.

(21) Appl. No.: 09/207,821

(22) Filed: Dec. 9, 1998

(51) Int. Cl.⁷ ...................................................... A61F 2/00
(52) U.S. Cl. ............................................................ 600/29
(58) Field of Search ........................................ 600/29, 30

(56) References Cited

U.S. PATENT DOCUMENTS

| | | | |
|---|---|---|---|
| 3,107,894 | 10/1963 | Quinn | 251/118 |
| 3,603,343 | 9/1971 | Keller | 137/493.6 |
| 3,731,670 | 5/1973 | Loe | 128/1 |
| 3,812,841 | 5/1974 | Isaacson | 128/1 |
| 4,553,533 | 11/1985 | Leighton | 128/1 |
| 4,616,672 | 10/1986 | Schmidt | 137/107 |
| 4,679,546 | 7/1987 | van Waalwijk van Doorn et al. | 128/1 |
| 4,742,846 | 5/1988 | DiBartolo | 137/514.5 |
| 4,792,335 | 12/1988 | Goosen et al. | 604/323 |
| 4,934,999 | 6/1990 | Bader | 600/29 |
| 4,949,746 | 8/1990 | Kay | 137/82 |
| 4,955,858 | 9/1990 | Drews | 604/8 |
| 4,968,294 | 11/1990 | Salama | 600/30 |
| 4,969,474 | 11/1990 | Schwarz | 128/885 |
| 5,007,894 | 4/1991 | Enhorning | 600/29 |
| 5,007,898 | 4/1991 | Rosenbluth et al. | 604/54 |
| 5,012,822 | 5/1991 | Schwarz | 128/885 |
| 5,041,092 | 8/1991 | Barwick | 604/104 |
| 5,078,676 | 1/1992 | Bailly | 600/31 |
| 5,088,980 | 2/1992 | Leighton | 600/30 |
| 5,090,424 | 2/1992 | Simon et al. | 128/885 |
| 5,097,848 | 3/1992 | Schwarz | 128/885 |
| 5,112,306 | 5/1992 | Burton et al. | 604/101 |
| 5,114,398 | 5/1992 | Trick et al. | 600/29 |
| 5,123,428 | 6/1992 | Schwarz | 128/885 |
| 5,140,999 | 8/1992 | Ardito | 128/885 |
| 5,203,372 | 4/1993 | Freiler | 137/469 |
| 5,512,032 | 4/1996 | Kulisz et al. | 600/29 |
| 5,570,713 | 11/1996 | Stoltz et al. | 137/12 |
| 5,624,374 | * 4/1997 | Von Iderstein | 600/29 |
| 5,676,181 | 10/1997 | Healy | 141/59 |
| 5,694,966 | 12/1997 | Holder | 137/115.11 |
| 5,713,877 | * 2/1998 | Davis | 600/29 |
| 5,722,932 | 3/1998 | Kulisz et al. | 600/29 |
| 5,884,623 | 3/1999 | Winter | 128/205.24 |

FOREIGN PATENT DOCUMENTS

WO 96/18431   6/1996   (WO) .

* cited by examiner

*Primary Examiner*—Max Hindenburg
*Assistant Examiner*—Brian Szmal
(74) *Attorney, Agent, or Firm*—Crompton, Seager & Tufte, LLC

(57) ABSTRACT

A valve for a bladder control device including an elongate housing having a valve seat disposed therein. A stopper is also disposed within the housing and is moveable between a first position in which the stopper engages the valve seat and a second position wherein the stopper is moved distally of the valve seat. A tension spring can be connected to the stopper to biases the stopper toward the valve seat. A lumen is defined through the housing having a first portion disposed distally of the valve seat having a diameter approximately equal to a diameter of the stopper. A second portion of the lumen disposed distally of the first portion has a greater diameter than the first portion of the lumen. Yet a third portion of the lumen disposed distally of the second portion has a diameter less than that of the first portion.

19 Claims, 3 Drawing Sheets

VALVE FOR BLADDER CONTROL DEVICE

BACKGROUND OF THE INVENTION

The present invention relates generally to the field of bladder control devices. More particularly, the invention relates to the field of bladder control devices in which a valve is provided to control flow from the bladder of a patient.

Bladder control devices related to the field of this invention include devices such as those disclosed by Kulisz et al., in U.S. Pat. No. 5,512,032 and U.S. Pat. No. 5,701,916. The former patent discloses a bladder control device including a valve which remains open under the influence of flow through the device in accordance with Bernoulli's Principle. The latter patent discloses proximally and distally disposed retainers for retaining the bladder control device within a patient's urethra. These pioneering devices can be activated in an intuitive way by a patient, simply by the patient increasing bladder pressure. The valve remains open at a lower pressure so long as a certain minimal flow rate through the valve continues. When the flow subsides, the valve closes.

Intraurethral bladder control devices are disposed within the urethra during use. Consequently, patients and their physicians desire that the diameter of the device be limited without compromising the performance of the device. It can be appreciated that larger diameter bladder control devices could cause some discomfort during insertion and use. Scaling down a device, i.e., making a smaller device having the same configuration, will reduce the flow through the device exponentially. Reducing flow through the valve limits the force creatable by the Bernoulli's Principle to hold the valve open. Additionally, if the diameter of a compression spring, as used in the prior devices to bias the valve close, is scaled down, the spring is subject to buckling, which could leave the valve in a permanently open position.

SUMMARY OF THE INVENTION

The present invention pertains to a valve for a bladder control device which incorporates features allowing the device to be effective when produced in small diameters, such as 18 F, for example. The valve for a bladder control device in accordance with the present invention includes an elongate housing which has a proximal end and a distal end. A lumen extends through the housing. A valve seat is disposed within the housing and a stopper is disposed within the housing. The stopper is moveable between a first position engaging the valve seat and a second position disposed distally of the valve seat. In the first position, the valve is closed, in the second position the valve is at least partially open.

The valve in accordance with the present invention, preferably includes a tension spring connected to a stopper to bias the stopper toward the valve seat. The spring is under greater tension loading when the stopper is in the second position that when the stopper is in the first position. The spring can include an elongate shaft portion having a proximal end and a distal end. The proximal end of the shaft portion is preferably connected to the stopper and the distal end of the shaft portion is preferably connected to a helical portion of the spring.

The stopper can include a proximal portion having a first diameter generally sized to engage the valve seat. The stopper preferably has a distal portion having a diameter greater than the diameter of the proximal portion.

The lumen through the housing can include a portion disposed distally of the valve seat having a diameter approximately equal to the diameter of the distal portion of the stopper. The stopper is preferably slidably disposed within this portion of the lumen for movement between the first and second positions. A second portion of the lumen, disposed distally of the first portion of the lumen, has a diameter greater than the diameter of the first portion of the lumen. The lumen also preferably includes a third portion disposed distally of the second portion of the lumen which has a diameter less than the diameter of the second portion of the lumen. This region of the lumen, in conjunction with the larger diameter distal portion of the stopper, can induce the desired force in accordance with Bernoulli's Principle to retain the stopper in the second position so long as a certain minimum flow rate through the lumen is maintained.

The housing in the valve of the present invention preferably has an outer diameter of between about 16 F to 22 F, and more preferably, about 18 F. It can be appreciated, however, that valves having greater or lesser outside diameters may also be made in accordance with the present invention.

DETAILED DESCRIPTION OF THE INVENTION

Figure 1:
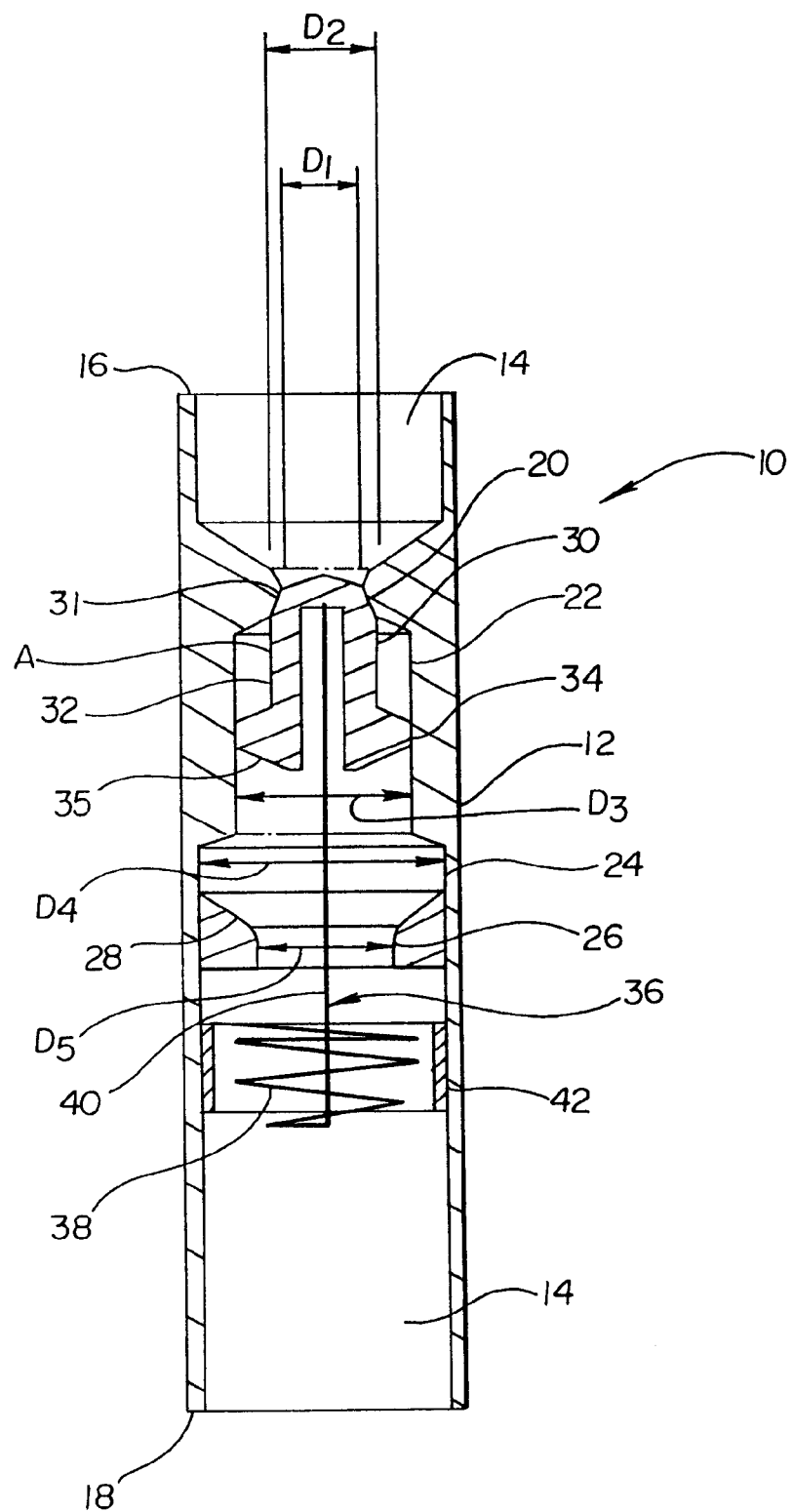
FIG. 1 is a cross sectional view of a valve in accordance with the present invention wherein the stopper is shown in engagement with a valve seat.

Referring now to the drawings wherein like reference numerals refer to like elements throughout the several views, FIG. 1 is a schematic cross sectional view of a valve 10 for a bladder control device in accordance with the present invention. Housing 12 can be formed from a biocompatible polymer, metal or other material. Housing 12 can be formed from a single piece or from an assembly of several pieces.

Valve 10 includes an elongate housing 12 having a lumen 14 extending therethrough from a proximal end 16 to a distal end 18. Valve 10 can be placed in the urethra of a patient. It can be retained within the urethra by proximal and distal retainers such as those disclosed in U.S. Pat. No. 5,701,916 to Kulisz et al. which is incorporated herein by reference. It should be understood, however, that the use of this valve is not limited to a configuration including the proximal and distal retainers of the referenced U.S. patent. It is contemplated that the valve could be used for bladder control of both male and female incontinence.

A valve seat 20 is disposed within housing 12. Valve seat 20 can be a narrow or constricted diameter region of the lumen 14. The diameter of seat 20 is $D_1$ (Radius, $R_1=D_1/2$). Distally of valve seat 20 is a first lumen portion 22 having a diameter $D_3$ (Radius, $R_3=D_3/2$). Lumen 14 includes a second lumen portion 24, disposed distally of first lumen portion 22, which has a diameter $D_4$ (Radius, $R_4=D_4/2$). Diameter $D_4$ is greater than diameter $D_3$. Lumen 14 also includes a third lumen portion 26 disposed distally of second lumen portion 24. Third lumen portion 26 has a diameter $D_5$ which is less than diameter $D_4$. Lumen 14 tapers along a slope 28 between second lumen portion 24 and third lumen portion 26.

Disposed within housing 12 is a stopper 30. Stopper 30 preferably has a proximal portion 31 configured for engagement with valve seat 20. Proximal portion 31 has a diameter of $D_1$. Disposed distally of proximal portion 31 is a portion 32 having a diameter $D_2$(Radius, $R_2=R_2/2$) less than $D_3$ of first lumen portion 22. Yet more proximally, stopper 30 includes a plunger portion 34 having a diameter approximately equal to, but less than $D_3$ of first lumen portion 22. Stopper 30 includes a sloping portion 35 sloping from plunger portion 34 to the distal end of stopper 30. Stopper 30 can be from a polymer, metal or other biocompatible material.

Disposed within housing 10 is a spring 36 for biasing stopper 30 toward valve seat 20. Spring 36 is preferably disposed distally of valve seat 28. Spring 36 is preferably a tension spring include an elongate shaft portion 40 having a proximal end connected to stopper 30 and a distal end connected to a helical spring portion 38. The opposite end of spring portion 38, not connected to shaft 40, can be affixed to housing 12 at, for example, a circumferential stop 42. Spring 40 can be made from stainless steel, NiTi alloy or other biocompatible material and suitable for the intended use.

A preferred relationship between $R_1$, $R_2$, $R_3$, and $R_4$ can be determined solving three equations. Assuming that $R_4$, the maximum inner diameter of lumen 14, is a given and that $\Delta R=R_2-R_1$, then $R_1$, $R_2$ and $R_3$ can be found using the following formulas:

$$R_1 = \frac{-\Delta R + \sqrt{3 \cdot R_4^2 - 2 \cdot \Delta R^2}}{3} \quad (1)$$

$$R_2 = R_1 + \Delta R \quad (2)$$

$$R_3 = \sqrt{R_1^2 + R_2^2} \quad (3)$$

The formulas given are preferred formulas, but can be viewed as exemplary. The length of first lumen portion 22 is preferably long enough that stopper 30 can move somewhat longitudinally therethrough without allowing flow through lumen 14. This could dampen spikes in bladder pressure without opening valve 10. This is an optional feature which is viewed as desirable.

Housing 12 preferably has an outer diameter of 14 F to 26 F, and more preferably between 16 F and 22 F, and most preferably, about 18 F. It can be appreciated that the valve described herein could also be scaled upward in size for other uses in addition to placement in the urethra. The configuration of valve 10 allowing for the production of relatively high flow rate valves disposed in housings having small outside diameters.

Figure 2:
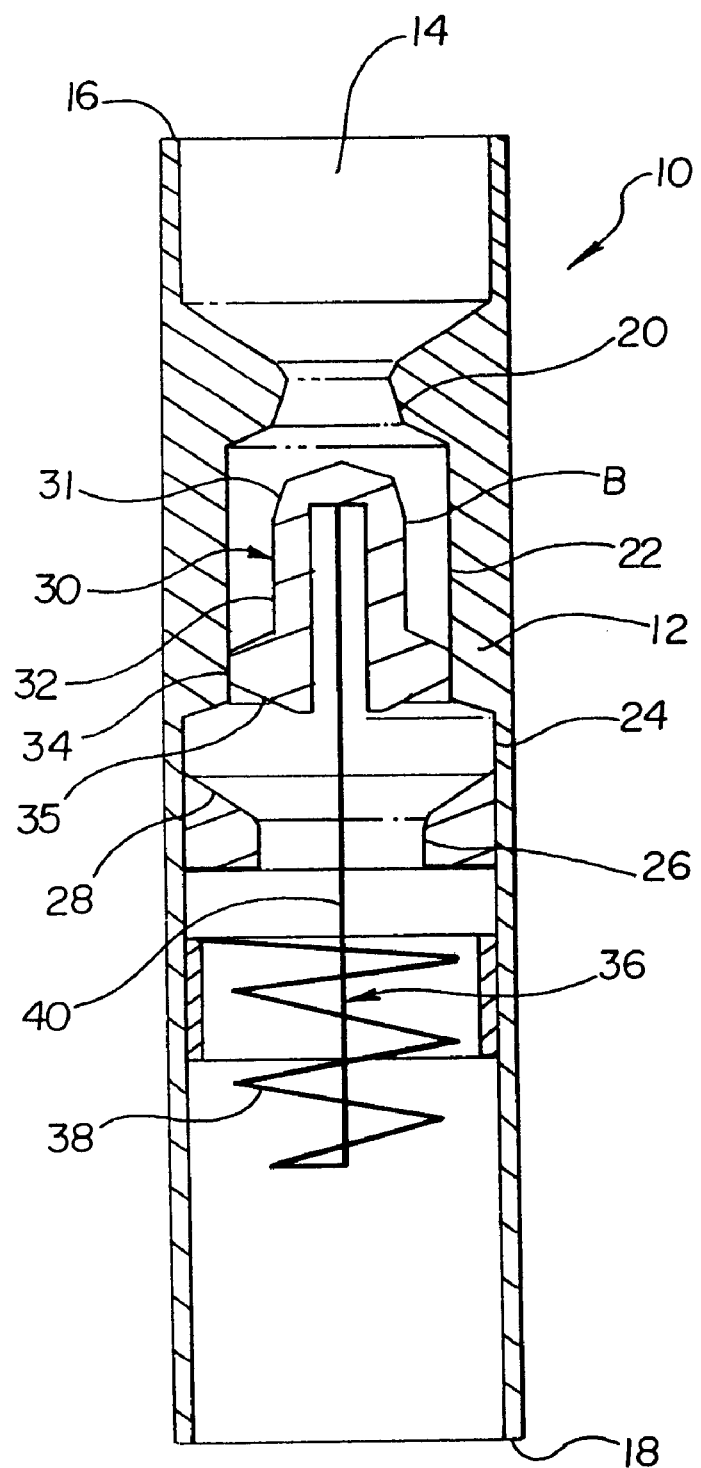
FIG. 2 is a cross sectional view of the valve of FIG. 1, wherein the stopper is moved distally away from the valve seat.

FIG. 1 shows stopper 30 in a first position A in which proximal portion 31 is in engagement with valve seat 20. FIG. 2 is a view of valve 10 of FIG. 1 in which stopper 30 is shown in a second position B. In position B, the pressure at the proximal end of valve 10 has increased enough to move stopper 30 away from valve seat 20. Stopper 30 is still, however, disposed within first lumen portion 22. The distal diameter portion 34 of stopper 30 engages the luminal wall of portion 22. Thus, there is still no flow through lumen 14, as is the case when stopper 30 is in engagement with seat 20.

Figure 3:
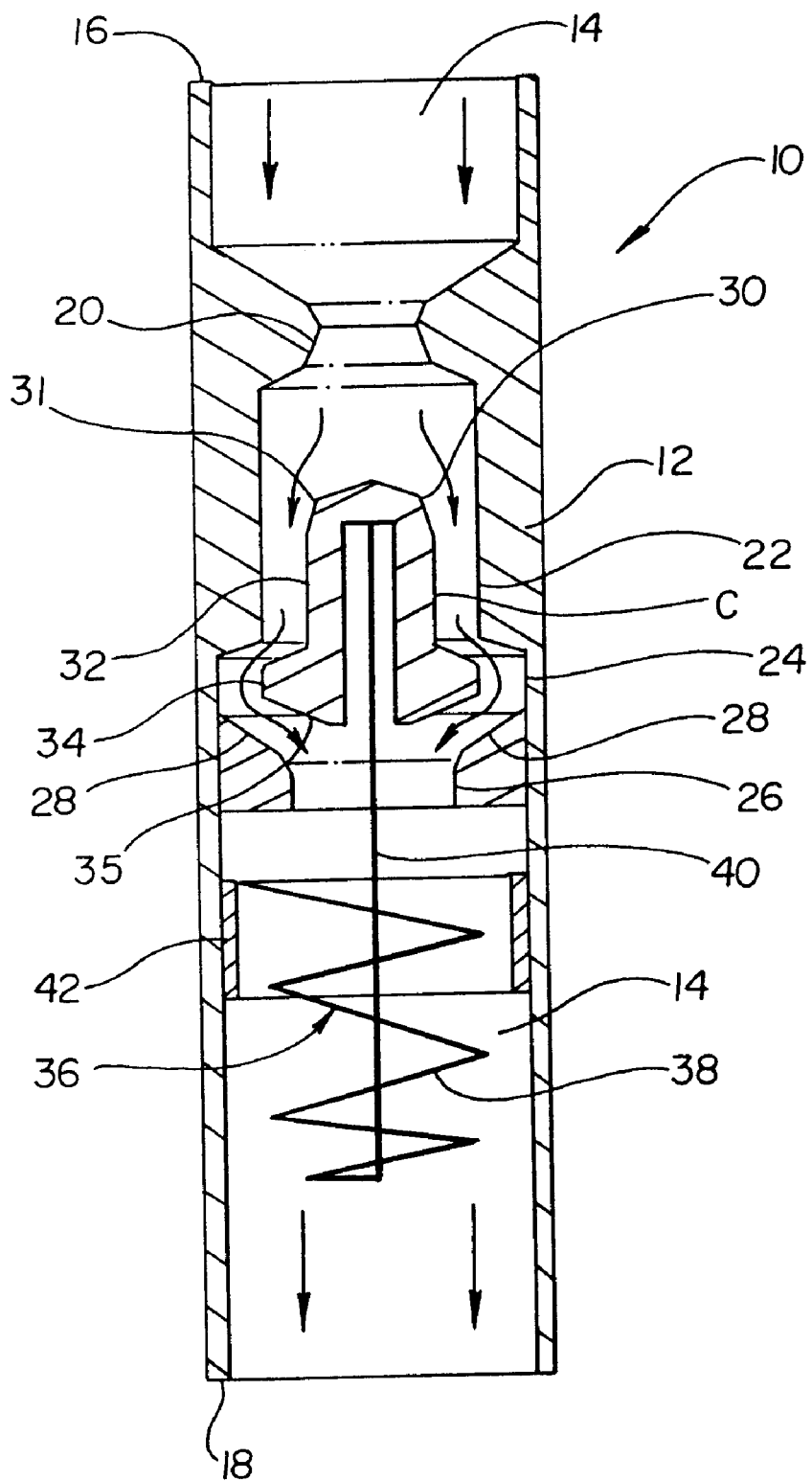
FIG. 3 is a view of the valve of FIG. 2, wherein the stopper is moved yet further distally to open the valve.

FIG. 3 is a view of valve 10 of FIGS. 1 and 2. In FIG. 3, stopper 30 is disposed in yet another second position C. In position C, portion 34 of stopper 30 is disposed within second lumen portion 24. Diameter $D_4$ of lumen portion 24 is sufficiently large to allow flow around plunger portion 34 of stopper 30, as shown by the arrows in lumen 14. In position C, the flow between slope 28 of lumen portion 24 and sloping portion 35 of stopper 30 can create a negative pressure in accordance with Bernoulli Principle. The negative pressure tends to draw stopper 30 in a distal direction. Once the flow subsides, however, the force generated in accordance with the Bernoulli Principle will cease and stopper 30 will move proximally toward valve seat 20. If the pressure in the proximal portion of lumen 14 is sufficiently low, stopper 30 will return to position A.

As can be seen in FIGS. 1, 2 and 3 as stopper 30 moves from position A to B and then to C, helical spring portion 38 elongates in a distal direction. Thus, rather than compressing portion 38, spring portion 38 is elongated under tension loading.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A valve for a bladder control device, comprising:
   an elongate housing having a proximal end and a distal end, and a lumen extending therethrough;
   a valve seat disposed within the housing;
   a stopper disposed within the housing and moveable between a first position engaging the valve seat and a second position disposed distally of the valve seat; and
   a tension spring connected to the stopper disposed to biases the stopper toward the valve seat, the spring being under greater tension loading when the stopper is in the second position than when the stopper is in the first position.

2. The valve in accordance with claim 1, wherein the spring includes a helical portion.

3. The valve in accordance with claim 1, wherein the spring is disposed distally of the stopper.

4. The valve in accordance with claim 3, wherein the spring includes an elongate shaft portion, having a proximal end and a distal end, the proximal end of the shaft portion being connected to the stopper, and the distal end of the shaft portion being connected to a helical portion.

5. The valve in accordance with claim 1, wherein the stopper includes a proximal portion having a first diameter.

6. The valve in accordance with claim 5, wherein the stopper includes a distal portion having a second diameter greater than the first diameter.

7. The valve in accordance with claim 6, wherein a first portion of the lumen disposed distally of the valve seat has a diameter approximately equal to the second diameter of the stopper and the stopper is slidably disposed therein for movement between the first and second positions.

8. The valve in accordance with claim 7, wherein a second portion of the lumen disposed distally of the first portion of the lumen has a diameter greater than the diameter of the first portion of the lumen.

9. The device in accordance with claim 8, wherein a third portion of the lumen disposed distally of the second portion of the lumen has a diameter less than the diameter of the second portion of the lumen.

10. The valve in accordance with claim 1, wherein the housing has an outer diameter of between 16 F to 22 F.

11. The valve in accordance with claim 10, wherein the outside diameter of the housing is approximately 18 F.

12. A valve for a bladder control device, comprising:

an elongate housing having a proximal end, a distal end, and a lumen extending therethrough;

a valve seat disposed within the housing;

a stopper disposed within the housing and moveable between a first position engaging the valve seat and a second position disposed distally of the valve seat, the stopper includes a proximal portion having a first diameter and a distal portion having a second diameter greater than the first diameter;

a spring connected to the stopper to bias the stopper toward the valve seat; and wherein a first portion of the lumen is disposed distally of the valve seat and has a diameter approximately equal to the second diameter of the stopper, and the stopper is slidably disposed in the first portion of the lumen for movement between the first and second positions, and a second portion of the lumen, having a diameter greater than the diameter of the first portion of the lumen, is disposed distally of the first portion of the lumen.

13. The valve in accordance with claim 12, wherein the spring comprises a tension spring being under greater tension loading when the stopper is in the second position than when the stopper is in the first position.

14. The valve in accordance with claim 12, wherein the spring includes a helical portion.

15. The valve in accordance with claim 12, wherein the spring is disposed distally of the stopper.

16. The valve in accordance with claim 15, wherein the spring includes an elongate shaft portion including a proximal end and a distal end, the proximal end of the shaft portion is connected to the stopper and the distal end of the shaft portion is connected to the helical portion.

17. The valve in accordance with claim 12, wherein a third portion of the lumen, disposed distally of the second portion of the lumen, has a diameter greater than the diameter of the second portion of the lumen.

18. The valve in accordance with claim 12, wherein the housing has an outer diameter between about 16 F to 22 F.

19. The valve in accordance with claim 18, wherein the outside diameter of the housing is approximately 18 F.

\* \* \* \* \*